United States Patent [19]

Ilsink

[11] Patent Number: Plant 5,916

[45] Date of Patent: Mar. 31, 1987

[54] ROSE PLANT

[75] Inventor: G. Peter Ilsink, Leersum, Netherlands

[73] Assignee: Jackson & Perkins Company, Medford, Oreg.

[21] Appl. No.: 775,992

[22] Filed: Sep. 13, 1985

[51] Int. Cl.[4] ..... A01H 5/00

[52] U.S. Cl. ..... Plt./2

[58] Field of Search ..... Plt./2, 5, 22, 26

*Primary Examiner*—Robert E. Bagwill

*Attorney, Agent, or Firm*—Manford R. Haxton

[57] ABSTRACT

A climber rose variety having vigorous climbing plant, blooming in large clusters on terminals and from laterals, throughout the growing season, of generally lavender color.

1 Drawing Figure

This present invention relates to a new and distinct variety of rose plant of the climber class which was originated by crossing the unpatented variety Yesterday with the unpatented variety Nastarana.

The primary objective of this breeding was to produce a new rose variety of the climber class, with ever-blooming capabilities, suitable for use in landscape or ground cover situations. This objective was substantially achieved along with other desirable improvements as evidenced by the following unique combination of characteristics which are outstanding in the new variety and which distinguish it from its parents as well as from all other varieties of which I am aware:

1. Plant blooms on short basal canes and repeats throughout the growing season;
2. Established plants produce canes 6′ or longer blooming in large clusters at the terminals;
3. Lateral shoots produce abundant blooms;
4. Blooms are small, nearly single; and
5. Bud and flower color is lavender.

Asexual reproduction of this new variety by cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:
- *Seed parent.*—Yesterday, unpatented.
- *Pollen parent.*—Nastarana, unpatented.

Classification:
- *Botanical.*—Rosa hybrid.
- *Commercial.*—Climber.

FLOWER

Observations made from specimens grown in a greenhouse at Irvine, Calif. in June.

Blooming habit: Continuous.

Bud:

- *Size.*—¾″ when petals start to unfurl.
- *Form.*—Long.
- *Color.*—When sepals first divide, between Red-Purple 66B and Red Purple 67C; when half blown, outer areas of outer petals between Red Purple 66B and 67C, inner area of outer petals between 66D and 67D to White at base of petals; inner petals, between Red Purple 66C and 67D; lower side of petals between 66A and 67B with large White area near base.
- *Sepals.*—Color: Near Green 138B. Three appendaged sepals lightly appendaged. Two unappendaged sepals hairy edge.
- *Receptacle.*—Color: Green 138B. Shape: Oval, Size: Relatively long. Surface: Hairy.
- *Peduncle.*—Length: Medium. Surface: Glandular. Strength: Stiff, slender.
- *Opening.*—Very fast from tight bud to flat.

Open bloom:
- *Size.*—Small. Average open size 1½″.
- *Borne.*—In clusters of 7 to more than 50, rounded.
- *Stems.*—Short, strong.
- *Form.*—When first open, flat. Permanence: Retains its form to the end.
- *Petalage.*—Number of petals under normal conditions: 11 to 15.
- *Color.*—Center of flower: outer areas of outer petals between Red Purple 66B and 67C, inner area of outer petals between 66D and 67D to White at base of petals; inner petals, between Red Purple 66C and 67D; lower side of petals between 66A and 67B with large White area near base. Base of petals, White. Major color: Red Purple 66C to 67D.
- *Variegations.*—None.
- *Discoloration.*—General tonality at end of first day: Same. Third day: Fades to Red Purple 68D.
- *Fragrance.*—Slight.

Petals:
- *Texture.*—Thin.
- *Shape.*—Sometimes notched, deltoid.
- *Form.*—Flat.
- *Arrangement.*—Imbricated. Petaloids in center, few.
- *Persistence.*—Drop off cleanly.
- *Lastingness.*—On the plant, fair. As cut flower, fair.

Reproductive parts:
- *Anthers.*—Small. Color: Golden yellow. Arrangement: Regular around styles.

*Filaments.*—Color: Yellow.
*Pollen.*—Gold yellow.
*Styles.*—Color: Reddish.
*Stigmas.*—Color: Yellow.

PLANT

Form: Climber.
Growth: Very vigorous, sprawly.
Foliage: Number of leaflets on normal mid-stem leaves: 5 or 7.
*Size.*—Medium.
*Quantity.*—Normal.
*Color.*—New foliage: Light Green overlaid with Greyed Purple 184B. Old foliage: Normally green.
Leaflets:
*Shape.*—Oval pointed.
*Texture.*—Leathery to glossy.
*Edge.*—Serrated.
*Serration.*—Single, small.
*Petiole.*—Rachis: Color: Green. Underside: With prickles.
*Stipules.*—Long, bearded.

*Disease resistance.*—Resistant to mildew, under normal growing conditions at Irvine, Calif.
Wood:
*New wood.*—Color: Light green. Bark: Smooth.
*Old Wood.*—Color: Green. Bark: Smooth.
Prickles:
*Quantity.*—On main canes from base: Ordinary. On laterals from main canes: Many.
*Form.*—Short, straight.
*Color when young.*—Brown.
Small prickles:
*Quantity.*—On main stalks, few. On laterals, few.
*Color.*—Brown.

I claim:

1. A new and distinct variety of rose plant of the climber class, substantially as herein shown and described, characterized particularly as to novelty by the unique combination of vigorous climbing plant, blooming in large clusters on terminals and from laterals, throughout the growing season, of generally lavender color.

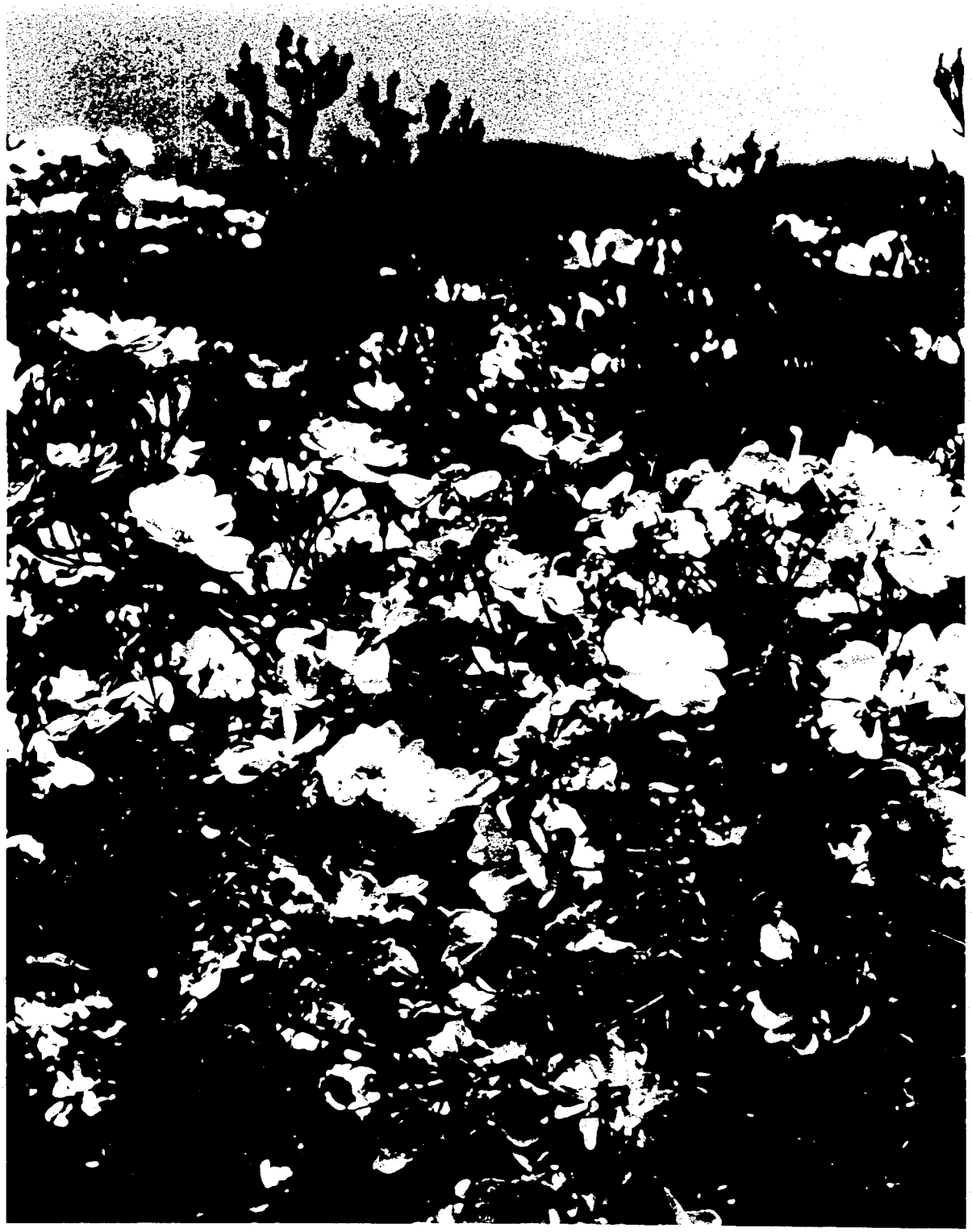

* * * * *